(12) United States Patent
Neev

(10) Patent No.: US 7,981,112 B1
(45) Date of Patent: Jul. 19, 2011

(54) HOME USE DEVICE AND METHODS FOR TREATING SKIN CONDITIONS

(76) Inventor: Joseph Neev, Laguna Beach, CA (US)

(*) Notice: Subject to any disclaimer, the term of this patent is extended or adjusted under 35 U.S.C. 154(b) by 448 days.

(21) Appl. No.: 11/752,893

(22) Filed: May 23, 2007

Related U.S. Application Data

(63) Continuation-in-part of application No. 10/150,632, filed on May 17, 2002, now abandoned, which is a continuation-in-part of application No. 09/694,738, filed on Oct. 23, 2000, now abandoned, which is a continuation of application No. 09/132,537, filed on Aug. 11, 1998, now Pat. No. 6,168,590, application No. 11/752,893, filed on May 23, 2007, which is a continuation-in-part of application No. 11/234,771, filed on Sep. 23, 2005.

(60) Provisional application No. 60/055,577, filed on Aug. 12, 1997, provisional application No. 60/802,960, filed on May 23, 2006, provisional application No. 60/921,901, filed on Apr. 4, 2007, provisional application No. 60/615,510, filed on Oct. 2, 2004, provisional application No. 60/678,968, filed on May 9, 2005, provisional application No. 60/704,602, filed on Aug. 1, 2005.

(51) Int. Cl.
*A61B 18/04* (2006.01)

(52) U.S. Cl. .......... 606/27; 606/28; 606/32; 607/98

(58) Field of Classification Search .............. 606/9
See application file for complete search history.

(56) References Cited

U.S. PATENT DOCUMENTS

| | | | |
|---|---|---|---|
| 5,207,671 A * | 5/1993 | Franken et al. | 606/9 |
| 5,571,216 A * | 11/1996 | Anderson | 128/898 |
| 5,620,478 A * | 4/1997 | Eckhouse | 607/88 |
| 5,630,811 A * | 5/1997 | Miller | 606/9 |
| 5,660,836 A * | 8/1997 | Knowlton | 424/400 |
| 5,720,894 A | 2/1998 | Neev | |
| 5,817,089 A | 10/1998 | Tankovich et al. | |
| 5,868,732 A | 2/1999 | Waldman et al. | |
| 5,879,346 A | 3/1999 | Waldman et al. | |
| 5,885,211 A * | 3/1999 | Eppstein et al. | 600/309 |
| 5,885,273 A | 3/1999 | Eckhouse et al. | |
| 5,906,609 A * | 5/1999 | Assa et al. | 606/9 |
| 6,050,990 A | 4/2000 | Tankovich et al. | |
| 6,134,475 A * | 10/2000 | Will | 607/98 |
| 6,156,030 A | 12/2000 | Neev | |
| 6,168,590 B1 * | 1/2001 | Neev | 606/9 |
| 6,228,082 B1 | 5/2001 | Baker et al. | |

(Continued)

FOREIGN PATENT DOCUMENTS
WO WO 02089688 A1 * 11/2002

*Primary Examiner* — Henry M Johnson, III
*Assistant Examiner* — Lynsey Crandall
(74) *Attorney, Agent, or Firm* — Richard B. Cates

(57) ABSTRACT

Skin tissue is subjected to thermal energy that creates heating of the area being treated causing pores and follicle ducts to open so that excess oil, sebum, fatty deposits, or other unwanted deposits can be removed. A vacuum device is used to direct suction to the treated skin area helping to remove the unwanted deposits. Patterned thermal modification of tissue is used to expedite healing and minimize pain. The heating is controlled so that no skin tissue is damaged while still providing enough heat to the skin to alter the flow of sebum and destroy bacteria in the treated area.

14 Claims, 10 Drawing Sheets

U.S. PATENT DOCUMENTS

| | | |
|---|---|---|
| 6,280,438 B1 * | 8/2001 | Eckhouse et al. ............ 606/9 |
| 6,402,739 B1 | 6/2002 | Neev |
| 6,408,212 B1 | 6/2002 | Neev |
| 6,482,199 B1 | 11/2002 | Neev |
| 6,508,785 B1 | 1/2003 | Eppstein |
| 6,685,699 B1 | 2/2004 | Eppstein et al. |
| 6,717,102 B2 | 4/2004 | Neev |
| 6,922,578 B2 | 7/2005 | Eppstein et al. |
| 7,020,528 B2 | 3/2006 | Neev |
| 7,163,536 B2 | 1/2007 | Godara |
| 7,244,253 B2 | 7/2007 | Neev |
| 7,494,492 B2 | 2/2009 | Da Silva |
| 2004/0005349 A1 | 1/2004 | Neev |
| 2005/0055055 A1 | 3/2005 | Neev |
| 2006/0074468 A1 | 4/2006 | Neev |
| 2006/0129214 A1 * | 6/2006 | Da Silva et al. ............ 607/109 |
| 2006/0142750 A1 | 6/2006 | DaSilva et al. |
| 2007/0255359 A1 | 11/2007 | Neev |

* cited by examiner

HOME USE DEVICE AND METHODS FOR TREATING SKIN CONDITIONS

This application is a continuation-in-part of U.S. application Ser. No. 10/150,632 filed May 17, 2002 now abandoned, which is a continuation-in-part of U.S. application Ser. No. 09/694,738 filed on Oct. 23, 2000 now abandoned, which is a continuation of U.S. application Ser. No. 09/132,537 filed on Aug. 11, 1998, now U.S. Pat. No. 6,168,590 granted Jan. 2, 2001, which claims priority to provisional application No. 60/055,577, filed on Aug. 12, 1997; and also is a continuation-in-part of U.S. application Ser. No. 11/234,771 filed Sep. 23, 2005 which claims priority to provisional patent application 60/615,510 filed Oct. 2, 2004, provisional application No. 60/704,602 filed Aug. 1, 2005, and provisional application 60/678,968 filed May 9, 2005; and still further claims priority to provisional application No. 60/802,960 filed May 23, 2006, and provisional application No. 60/921,901 filed Apr. 4, 2007; all of which are incorporated herein in their entirety by reference.

FIELD OF THE INVENTION

The present invention relates generally to the application of energy to biological tissue, and specifically to the application of electromagnetic energy to the skin in order to treat various skin diseases.

BACKGROUND

It is known in the art to apply electromagnetic energy to biological tissue to engender changes therein. Sunbathers, for example, regularly expose themselves to bright sunlight in order to increase melanocyte activity in the basal layer of the epidermis, responsive to the sun's ultraviolet (UV) radiation. Artificial UV sources have been created to satisfy the desire for a healthy-looking tan in the winter. Other forms of electromagnetic energy, laser-light in particular, are currently used in a large range of therapeutic and cosmetic procedures, including eye surgery, hair removal, wrinkle removal, and tattoo removal.

PCT publication WO 98/55035, which is incorporated herein by reference, describes methods for minimizing injury to biological tissue surrounding a site exposed to pulses of electromagnetic energy. This and all other extraneous materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

U.S. Pat. No. 5,720,894 to Neev et al., which is incorporated herein by reference, describes biological tissue processing using Ultrashort Pulse High Repetition Rate Laser System for Biological Tissue Processing.

It is known in the art to use UV and blue light to cure acne. A beam of short wavelength light is irradiated and is supposed to destroy bacteria through sterilizing ability of the high energy photon to disrupt molecular bond and photochemical destruction of living cells. This method is deficient however, because of the relatively short depth of penetration of the short wavelengths regime and the danger of mutagenetic effect as well as the effective shielding of deeper lying bacteria by superficial skin structures.

It is also known in the art to use chemical peels and Retin A to chemically peel of the outer layer of the skin. This method is deficient however, because of side effect, long response time and longer time duration between application of the treatment and results and various side effects.

It is also known in the art to apply antibiotic to patients in order to combat active acne. This method is deficient however, since the application of antibiotic is non-selective, often done systemically and thus effect the entire body, and also for the fact that various organisms and bacteria develop resistance to antibiotics and in fact, expose the entire body to increase danger in exposure to bacteria that is now resistance to antibiotics.

It is also known in the art to combat active acne by treating and controlling hormonal activity within a patient body. Again, this is a systemic approach that suffers from many side effects including, in some cases, severe depression, and impact on the entire body.

It is therefore, desirable, to have a simple, non-invasive, non-systemic treatment method and apparatus for the treatment and cure of acne, that, when applied, are free of side effect, yet safe and effective. It is also desirable to have a method that is easy to apply and is relatively quick and easy to administer and produce rapid skin response, relief of symptoms, and cure for the condition.

It is also desirable, to have a simple, safe, non-invasive, non-systemic treatment method and apparatus for the treatment and cure of other skin diseases and skin conditions, that, when applied, are free of side effect, yet safe and effective. Finally, it is particularly desirable to have a safe home use small and compact device that consumer can carry with them or use in the home or office environment for treatment of pimple, acne, or minor skin conditions, with or without the application and use of medicine or topical medication, to resolve irritating skin conditions including acne.

SUMMARY OF THE INVENTION

The present invention provides methods and apparatus in which a region of intact living skin is treated with energy pulses having a duration of short duration, at an average energy density such that a temperature at the surface rises to at least 45° C. without substantially denaturing tissue at the epidermal/dermal junction. The basic principle is to heat up the surface of the skin with sufficient heat to cause opening of the pores, but limit the amount of energy to such that when it is diffused and distributed over a larger volume (in the dermis), the energy is below that which would cause substantial denaturation of cells in the skin.

In especially preferred embodiments the energy pulses are produced by an electric heater coupled to a capacitor and a battery, the capacitor discharge between 0.2 J/cm2 to 10 J/cm2 and preferably between 0.5 J/cm2 and 5 J/cm2 and most preferably between 0.7 J/cm2 and 3 J/cm2 in pulse of between 0.1 ms and 10 ms. The energy pulses are preferably radiates electromagnetic radiation that includes visible wavelengths.

To avoid overheating of, and damage to, the dermis and underlying tissues, the pulses have durations of less than 30 seconds, more preferably less than 10 seconds, and in some cases less than 1 second, less than 0.1 sec, or even less than 0.01 sec. Pulses can be repeated at any desirable frequency, including especially between 0.5 second and 10 seconds, and more preferably between about 2 second and 5 seconds. Unless a different meaning is dictated by the context, all ranges herein should be interpreted as being inclusive of their endpoints. Interpulse delays of between 0.2 sec and 10 sec are preferred, with interpulse delays of between 2 sec and 5 sec even more preferred. Thus, it is contemplated that the controller could cooperate with the energy source to subject the treatment region to at least 2 of the energy pulses within a 20 second period, and possibly at least 10, 25, 50, 75 or even a hundred such energy pulses within a 20 second period.

In other aspects of preferred embodiments, the tip treatment area is preferably between 0.2 mm and 10 cm in diameter, and preferably between about 2 mm and about 2 cm in diameter.

From a method standpoint, it is contemplated to operate a device as described herein such that hair follicles in the skin expand without being permanently damaged. By appropriately selecting pulse energy density, pulse width, and inter-pulse delays, it is possible to raise the surface temperature of the skin at least 60° C. or even 70° C. or more without substantially denaturing tissue at the epidermal/dermal junction. In some cases this effect can be facilitated by actively cooling the surface of the skin to a temperature of less than 50° C.

It is still further contemplated that operation of devices as described herein can include treating the skin with anti-microbial radiation that includes blue to ultraviolet wavelengths (to achieve an antimicrobial effect), and applying a vacuum to the skin within 5, 10, or 15 minutes of application of the pulse (to help remove debris released during the heating portion of the treatment).

In a preferred embodiment of the present invention, the tissue of the skin is subjected to localized heating that for a given time and in a defined location, elevates the temperature of the skin in one location as compared to an its normal temperature. This elevation of skin temperature corresponds to expansion and displacement of a portion of the skin thus leading to opening of skin pores.

In another preferred embodiment of the present invention, the tissue of the skin is subjected to localized heating that for a given time and in a defined location, elevates the temperature of the skin in one location as compared to an adjacent location. This elevation of skin temperature corresponds to expansion and displacement of a portion of the skin with respect to an adjacent location thus leading to opening of skin pores.

In a further preferred embodiment, an intermediate substance which is capable of absorbing at least a portion of the electromagnetic energy from a source, is placed between the energy source and the skin, absorbs the source energy and converts it to heat. Being in contact with the skin, the substance elevates the temperature of the skin to cause to an expansion and displacement leading to opening of skin pores and relieving of acne conditions.

In yet a further preferred embodiment, an intermediate substance which is capable of absorbing at least a portion of the electromagnetic energy from a source, is placed between the energy source and the skin, absorbs the source energy and converts it to heat. Being in contact with the skin, the substance elevates the temperature of the skin in one location as compared to an adjacent location. This elevation of skin temperature corresponds to expansion and displacement of a portion of the skin with respect to an adjacent location thus leading to opening of skin pores.

As will be apparent from the description contained herein, aspects of the inventive subject matter include:

a. Providing an improved apparatus and methods for applying energy to a material;
b. Providing improved apparatus and methods for removing heat generated during application of electromagnetic energy to a material;
c. Providing improved apparatus and methods for removing heat generated during application of electromagnetic energy to biological tissue;
d. Providing improved apparatus and methods for decreasing pain during application of electromagnetic energy to biological tissue;
e. Providing improved apparatus and methods for performing medical treatments;
f. Providing improved apparatus and methods for performing cosmetic treatments;
g. Providing improved apparatus and methods for healing of skin diseases and skin illnesses;
h. Providing improved apparatus and methods for enabling electromagnetic energy source to allow healing of skin diseases and skin illnesses or improved conditions;
i. Providing methods and apparatus for enabling a chemical, RF, Microwave, mechanical, electric, magnetic, or ultrasound energy to advance healing skin diseases and skin illnesses;
j. Providing improved methods and apparatus for enabling a low-power electromagnetic energy source to advance healing skin diseases and skin illnesses substantially without pain, while substantially minimizing the amount of damage or modification to remaining tissue;
k. Providing improved methods and apparatus for enabling a low-power electromagnetic energy source to perform skin treatment, treatment of acne and treatment that prevent the occurrence of acne;
l. Providing improved methods and apparatus for enabling a low-power electromagnetic energy source to perform tissue treatment that cures acne and relieves symptoms of acne.

These and other objects, features, aspects and advantages of the inventive subject matter will become more apparent from the following detailed description of preferred embodiments, along with the accompanying drawings in which like numerals represent like components.

DETAILED DESCRIPTION

Figure 1A:
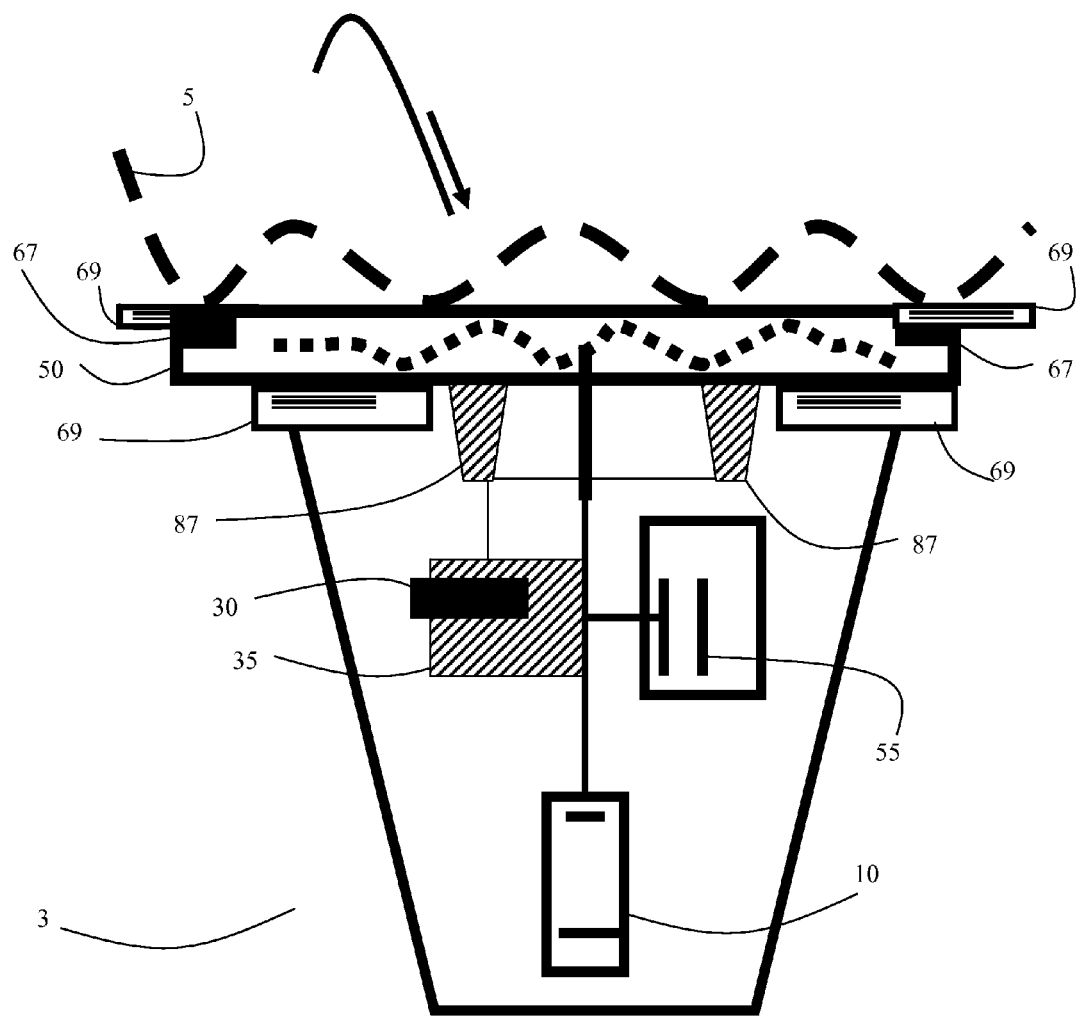
FIG. 1A is a simplified diagram of an apparatus for treatment of acne and skin condition and its components.

Devices and methods are contemplated herein for treatment of a variety of skin conditions, and in particular, cyst, acne, aged skin, and wrinkles. In FIG. 1A the device 3, designed to treat a skin surface 5, comprises the following components: an energy source 10, for example, a battery, an electro-mechanical dynamo, or an electric wall outlet, among other possible energy sources, that provide energy to the device control elements 30 for example a control element on a circuit board 35. The control elements are 30 are activated by an input switches (not shown), for example, a power level switch, a trigger switch, and an off/on switches, that allow the users to interface with the device, for example they allow the user to control the operation, power level and activation of the device. The control element 30, allows the energy source to power the treatment head 50, directly or to charge up a plurality of capacitors 55 or other intermediate elements (resistors, diodes, etc.) that modify the energy output of the treatment heads. The treatment head 50 can include a resistor that provides heating to the skin by diffusion.

Figure 1B:
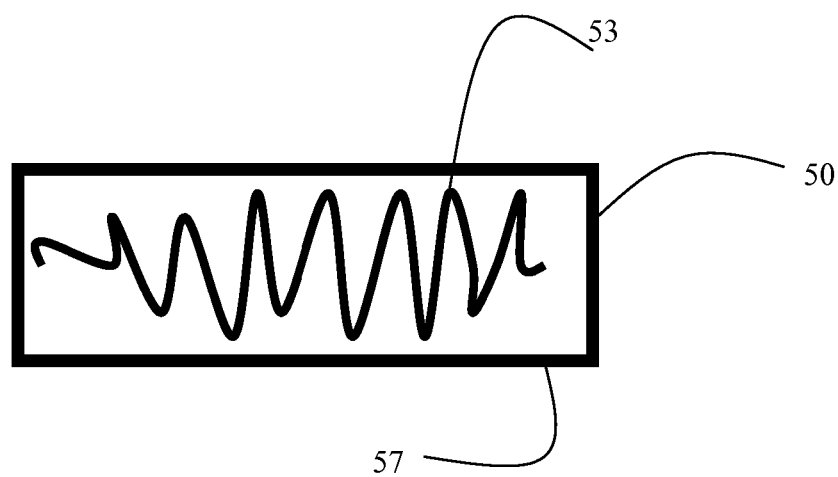
FIGS. 1B and 1C are simplified diagrams of contemplated heating elements.
Figure 1C:
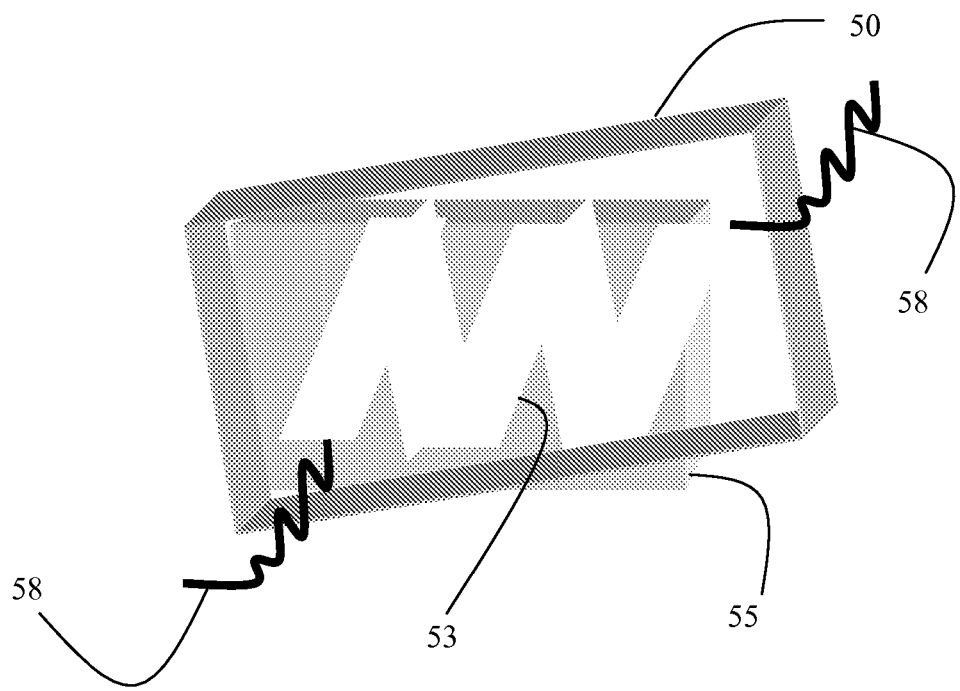

In preferred embodiments of FIGS. 1B and 1C, the treatment head 50 can be made from a heating element, for example a resistor 53 can be embedded in an insulating material 57 for example Teflon or a plastic material that is sufficiently thin to allow rapid conduction of the thermal energy to the skin. In another preferred embodiment, the resistor can be made of a conductor in a flat configuration so that it conduct heats uniformly in as a planar configuration of temperature gradient as shown in FIG. 1C. This will allow the heat to diffuse as a flat planar diffusion of thermal energy front to the skin. The resistor can be mounted on a layer of glass or Teflon, plastic, or other insulating material 57, which reduces removal of thermal energy from the resistor, and facilitates diffusion of the thermal energy by conduction towards the targeted skin. Between the resistor and the target skin one can advantageously include a thin layer of electrically insulating material 57 that prevents electricity from the resistor from reaching the skin but allows thermal energy from the resistor to reach the skin. The resistor can be made of typical material known in the art such as copper, aluminum, tungsten, steel, Nichrome™, or copper and tin alloys.

Resistors can advantageously be coated with a thin layer of electrically insulating layer but thermally conducting material that allows the heat to flow but prevent electric current from reaching the skin—for example by anodizing processes. The treatment head 50 can have any suitable thickness, preferably 10 micrometer to 1 mm, more preferably between 25 micrometer and 500 micrometer, and most preferably between 50 micrometer and 200 micrometer. The electrical insulating layer 57 can also have any suitable thickness, preferably between 5 micrometer and 1 mm, more preferably between 10 micrometer and 500 micrometer, and most preferably between 20 micrometer and 250 micrometer.

Because the maximum amount of energy that is loaded up onto the heater element is the maximum amount of energy (or heat) available to treat and also to possibly cause excessive collateral damage, it determine the upper limit of the risk of the method and the device contemplated herein. The upper limit of the amount of energy in provided by the resistor is determined by its heat capacity (for example, the most energy a heating element can have is if the full amount of energy from a discharging capacitor, $0.5\ CV^2$. If the heating element is completely insulated, and is designed to reach a temperature increase DT above normal skin temperature (for example, if we design DT=200° Centigrade), then the amount of energy that will allow it reach that temperature is determined by the heat capacity of the heating element. The heat capacitance is a function of the heating element volume and hence for a designed treatment area (for example between about 0.2 cm$^2$ to about 9 cm$^2$ and preferably, 2 cm$^2$) a thinner heating element will have smaller heat capacitance and hence will store less energy corresponding to its designated temperature DT. Thus by proper design of the heat capacitance and thickness of the heater, we can calculate and limit the upper value of energy available for transfer into the skin. For this reason, a thin heater will serve to limit the amount of energy available for heating of the skin. For example, a total thickness of the heating element 50 should be between 20 micrometer and about 500 micrometer, and preferably between about 30 micrometers and about 300 micrometer. The wires 58 provide current to the resistive heating element 53.

A temperature monitoring element (for example, a thermo couple or an IR detector, for example, HgCd detector) can be integrated into the heating element as shown in FIG. 1, and be operatively coupled to the heating element 67. A cooling element 69, for example a TEC, can also be integrated into the treatment head to reduce the temperature of the treatment head before the next shot if fired. For example, a reduction to temperature range between about 25° C. to 45° C., and preferably between about 27° C. and about 37° C., can be required before the device can be fired again.

Figure 1D:
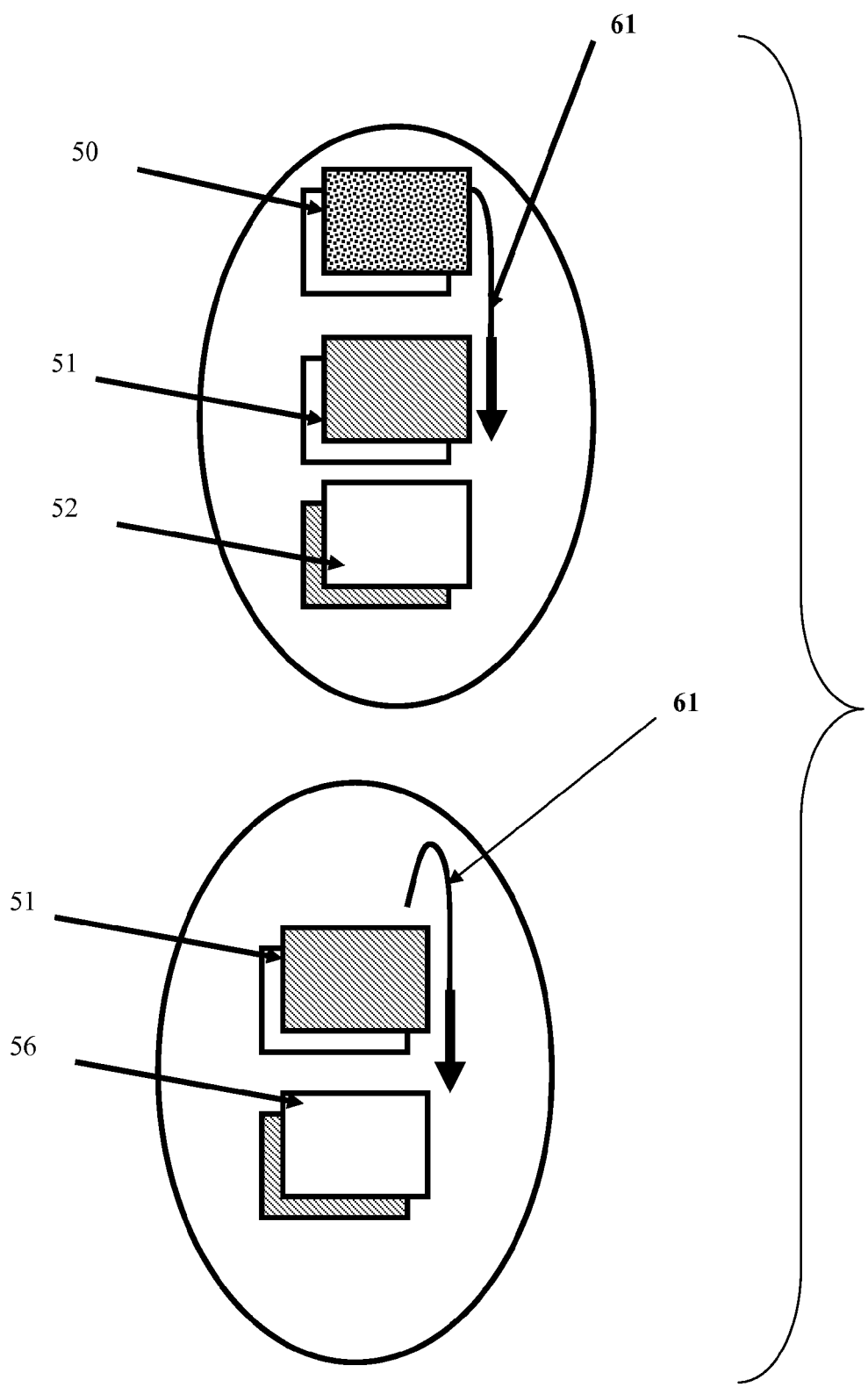
FIG. 1D is a simplified diagram of an array of heating elements.

As shown in FIG. 1D, a plurality of treatment heads can be used. Thus, heads 51, 52 can be used while treatment head 50 is cooling. For convenience, the treatment heads 50, 51 and 52 can all be mounted on a conveyer belt or other actuator, and thereby moved in the direction of the arrow 61.

Figure 1E:
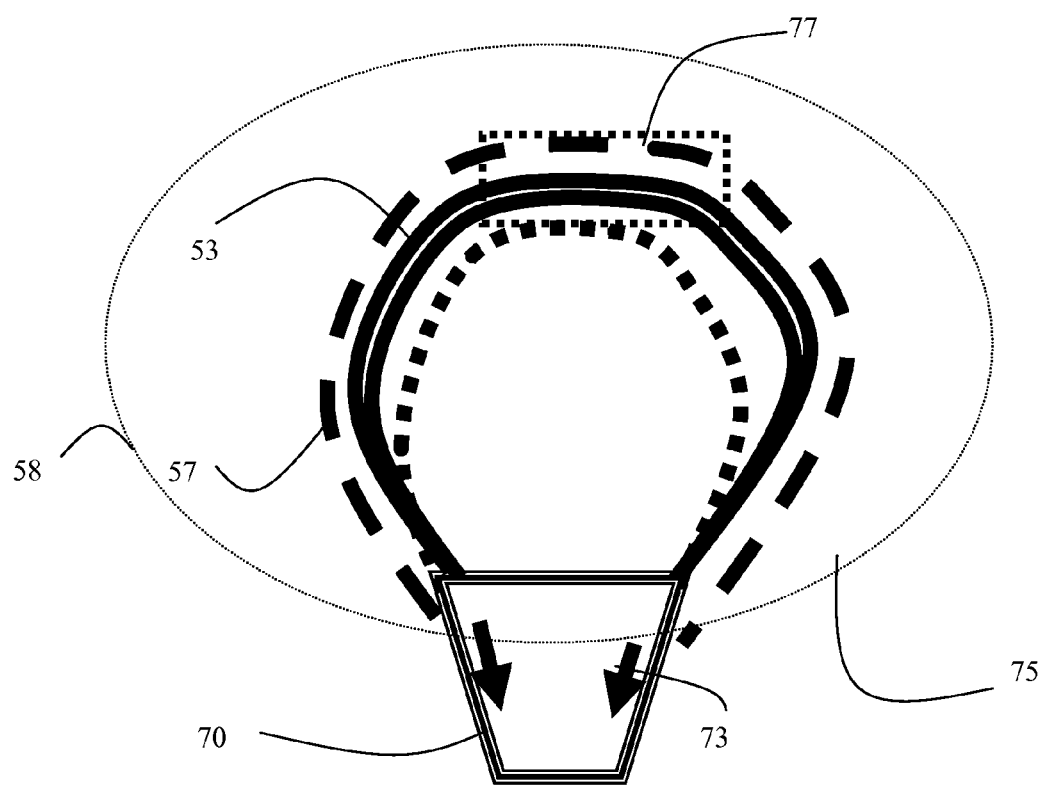
FIG. 1E is a simplified diagram of an alternative treatment head.

In FIG. 1E an alternative treatment head 75 includes heating element 53 mounted on insulating material 57 and ultimately flexible layer 58. Treatment head 75 is flexible, and is mounted on a collapsible/extendable rack 70, which can be extended or expanded in the direction of the arrows 73, pulling with it the entire assembly of treatment head 75, over respect to a variable treatment area 77. The variable size treatment area 77 can range, for example, from about 0.5 mm in diameter to about 5 cm in diameter, and preferably from about 2 mm in diameter to 25 mm in diameter.

The above treatment head cooling and adjustable head size may not be necessary if a simple handheld device is need. Thus, in general, a preferred embodiment includes a device for treatment of skin conditions comprising: an energy source adapted and configured to provide energy to the skin surface; and a controller adapted and configured to automatically energize the energy source so it heats the skin to a temperature sufficient to loosen, dislodge destroy or otherwise desirably modify the blockage within the follicle so as to allow drainage thereof in response to a user input.

Heating elements can be coated for several reasons, including to enhance safety, provide quicker temperature changes, and for improved patient experience. For example, as shown in FIGS. 1B, 1C a resistor 53 can be embedded in an insulating material 57. For example, Teflon or other plastic or glass electrically insulating material that allow the heat to thermally conduct and reach the skin, 5, can be used. In some contemplated embodiments a thin electrically insulating coating (for example, a thin plastic coating can be applied or an anodizing process can be used) can be applied to the resistor to prevent electrical current from reaching the skin, while still allowing heat to diffuse and reach the skin.

It is contemplated that controller 30 can operate to cease providing energy to the heating element, and to reheat the heating element without a further user input.

It is also contemplated that energy provided to the skin can causes substances inserted in the hair follicle to expand.

It is also contemplated that the energy source and controller can be co-located in a housing, and that the housing can be sized and dimensioned to be hand held.

One or more energy removal elements 69 may also be used. The energy removal element should be adapted and configured to cool said heating element and/or a skin surface to a temperature of less than about 50.degree C., and an electromagnetic source of energy in the blue to ultraviolet range is also applied to achieve sterilization of the skin.

Particularly preferred methods and apparatus include: a heating element adapted and configured to contact a skin surface; and a controller adapted and configured to automatically heat the heating element to a temperature sufficient to loosen, dislodge destroy or otherwise desirably modify the blockage within the follicle or improve the condition and health of the skin in response to a user input. Such devices can advantageously raise the temperature surface of the skin ifs to above 38° C., more preferably to above 45° C., and in some cases could transiently raise the temperature of the surface of the skin to 70° C., or even 100° C., 200° C., 250° C., 300° C., 350° C. or more.

Of course, such high temperatures would be maintained for only a short period of time, to avoid substantial permanent damage to the majority of the living cells in the skin. Thus, the contemplated devices and methods would preferably not be applied in an ablative manner. To that end elevated heating of the surface of the skin would typically occur for a heating period that is less than about one second, more preferably less than about 0.1 second more preferably yet less than about 0.01 second and most preferably less than about 1 ms.

Also contemplated herein are methods of treating a subject having a skin lesion, comprising applying energy to a lesion; heating the lesion to a temperature sufficient to modify skin condition and treat disease but cause serious burn; and repeating the energy applications and heating steps at least one time.

Figure 2:
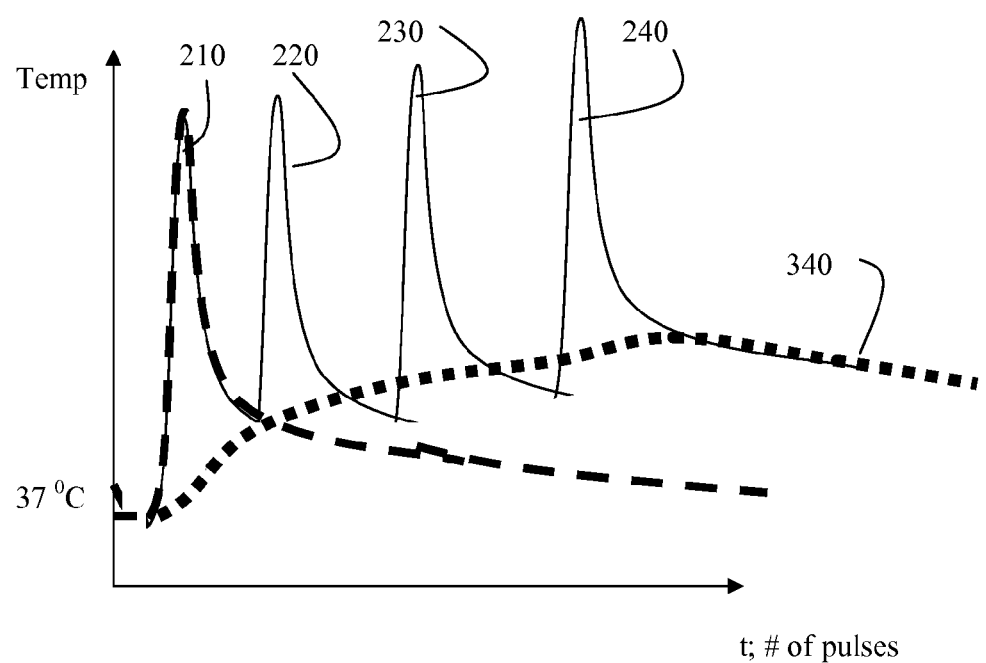
FIG. 2 is a simplified diagram showing a representative heat accumulation and temperature vs. pulse number effect on the skin surface.

For example, if an electric current is used to heat up a resistor, for example by charging up and discharging a capacitor through the resistor as is contemplated by one preferred embodiment, or, for example, by providing a DC or AC current through the resistor adapted to contact the skin, and using automated or manual interruption to terminate the current flow and heating phase, then repeating the heating cycle will result in accumulation of heat in the skin and temperature build up, for example, as shown in FIG. 2.

As shown in FIG. 2 the temperature of the skin due to the first heating cycle 210 is reach a peak temperature, for example, 300° C., and then decays to lower values due to conduction to the skin and some loss to the insulating material 57 of FIG. 1A. A second pulse, for example a few seconds later may raise the temperature of the skin which has not yet been able to decay to its normal ambient temperature, for example, 37° C., and for example has only reached a lower temperature of 45° C., will now rise again due to cycle number 2, for example to a peak temperature of 310° C. as sown in 220. A third pulse will raise the pick temperature for example to 320° C. peak and will decay to a temperature of, for example 50° C. We can see that the accumulation of thermal energy from repeated heating cycles 1, 2 and 3 as shown by the curves 210, 220, 230 and 240 will result in a slow average skin temperature rising as shown by the curve 340 from its ambient exemplary 37° C. to an elevated 50° C. The tail of the curve 210 (broken line) shows what the decay of a single pulse will look like.

The number of such repeated heating cycles should there be limited or space apart by several seconds to allow cooling between pulses, or utilize active cooling such as Thermoelectric (TEC) cooling or cryogen spray cooling incorporated with the method or device to prevent accumulation of excess cooling of the skin surface that can lead to deeper tissue effects or burn. The heating step if done through a slower heating process should be limited in time or monitor with the thermocouple 67 of FIG. 1. If limited in time this preferred embodiment heating step should preferably be limited to less than 3 minutes, more preferably to less than 1 minute, more preferably yet to less than 30 second, more preferably yet to less than 1 second, more preferably yet to less than 100 ms, more preferably yet to less than 10 ms, more preferably yet to less than 1 ms, and more preferably yet to less than 0.1 ms.

In an additional preferred embodiment, an electrical device for the treatment of skin lesions comprising: (a) an interface for contacting the skin of a subject; (b) a heater capable of heating the interface to a temperature sufficient to cause expansion of the hair follicle and treatment of skin conditions without irreversible damage to living cells. The device may optionally include an energy removal (i.e., cooling) element 69, preferably capable of cooling the heating element and/or treatment surface to a temperature of less than about 50° C. Still further, the device may include a source of electromagnetic energy 87 in the blue to ultraviolet range, which can be applied to at least partially sterilize the skin.

Figure 3:
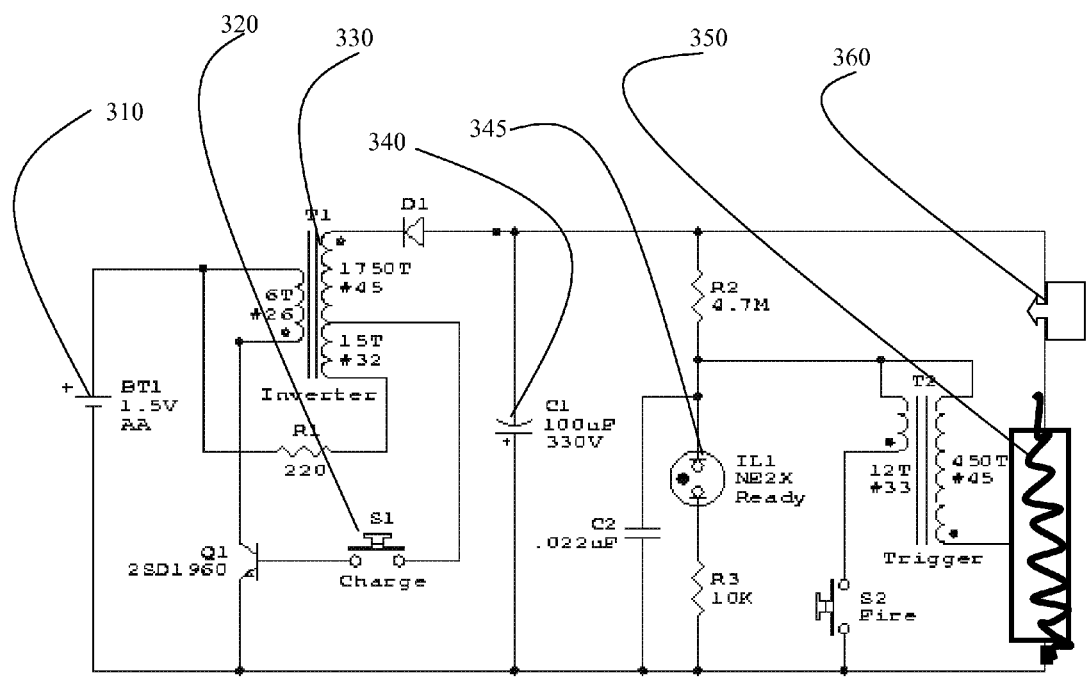
FIG. 3. is a simplified diagram of a possible circuit diagram for an eclectic heater skin and acne treatment device.

FIG. 3 shows one possible circuit diagram to pulse a flash lamp 350. A switch 320 is turned on to draw power from battery 310, through transformer 330, to activate the device and charge the capacitor 340. When the capacitor is fully charged a lamp 345 (or LED) is turned on and the circuit is ready to fire. Push button 360 is pressed to discharge capacitor 340. After firing, the capacitor 340 begins to charge, and after several seconds (depending on battery and resistance) is fully charged. This circuit releases a maximum energy per pulse of ½ $CV^2$ where is the capacitor capacitance and V is the final voltage across the capacitor. By selecting appropriate values of C, and V the released energy can be kept at the appropriate level so it loads up sufficient amount of energy into the top layer of the tissue (for example a discharge of time of 1 ms will allow diffusion into about 30 micrometer of tissue with thermal conductivity similar to that of water, thus the amount of energy in this tissue should be enough to cause temperature jump high enough to cause sufficient tissue expansion so that pores and spacing in the epidermis are opened to allow healing of acne and other skin conditions. However, the amount of energy discharged and conducted into the tissue is not enough to cause serious collateral damage or serious burn because the total amount of energy per unit volume conducted into the deeper tissue, i.e. less than ½ CV2, is too low to interact with the living cells and cause significant irreversible damage or serious burn).

Figure 4:
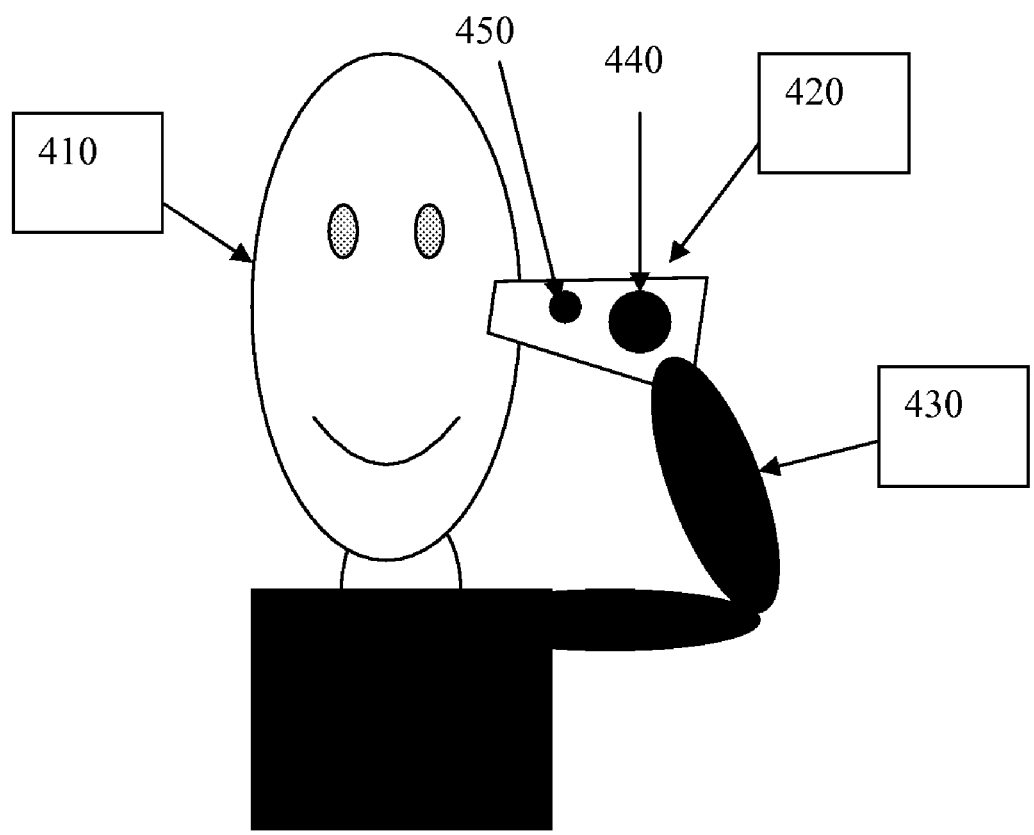
FIG. 4. is a simplified diagram showing how a handheld skin treatment device is used to treat the skin.

FIG. 4 shows how the device can be used by a consumer suffering from acne or other skin conditions. The use 410 holds the device 420 in his hand 430, and push a charge button 440 to initiate charging and a fire button 450 to fire the device once it has made a good contact with the user face, 410.

Figure 5:
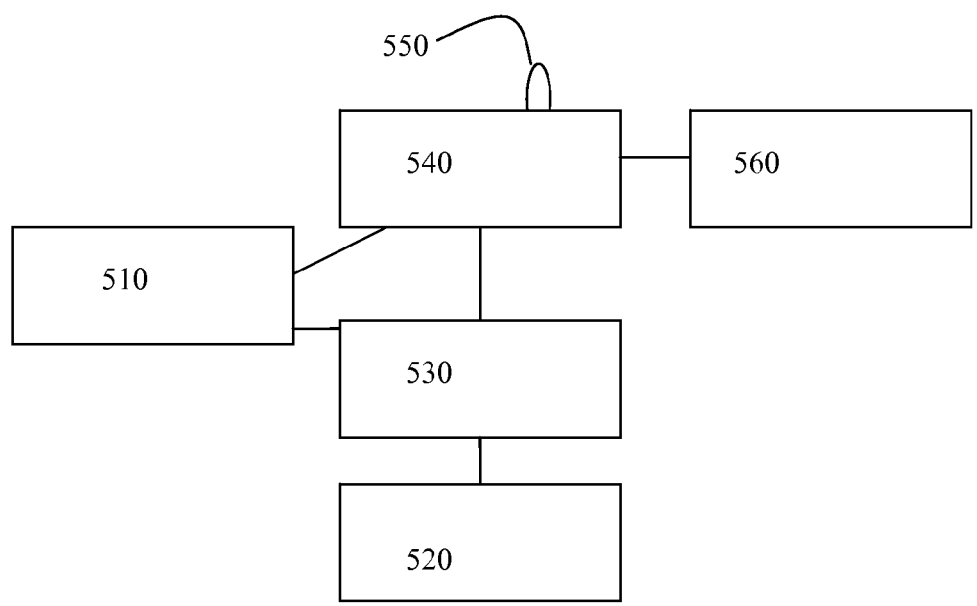
FIG. 5 is a simplified diagram is a block diagram for a device components

In FIG. 5, 510 is a source of energy, for example, a battery or a wall plug; 520 is a user interface such as power control, a charge button and a fire button; 530 is a microprocessor powered by the power source such as a battery and controlling the firing sequence, charging times, firing repletion rate, and power levels, responsive to the user input; 540 is a capacitor and pulse generator assembly capable using the power source power to charging the capacitor and storing the electrical energy; 550 is the full charge indictor telling the user that the device is ready to fire and 560 is the heater adapted to contact the skin to heat the surface to the required level.

An additional preferred embodiment of the present invention contemplates a device for treatment of a skin conditions and acne: an energy source adapted and configured to provide energy to the skin surface; a controller adapted and configured to automatically energize the energy source so it heats the skin to treat said skin conditions and acne, and a vacuum source to be applied to the skin before, during or after the energy application to said skin. In a preferred embodiment, an energy source, for example a laser or a broad lamp, flash lamp or an RF energy source, an ultrasound beam or microwave energy source is applied to the skin.

Figure 6:
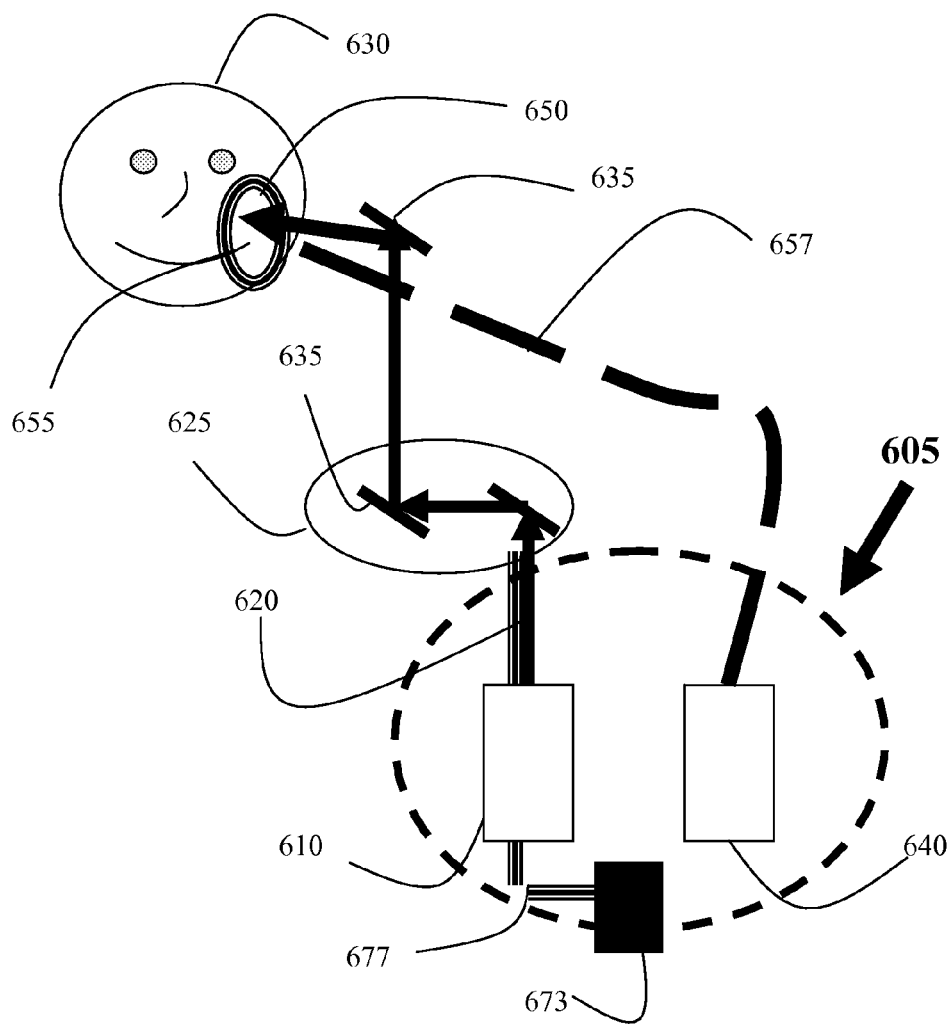
FIG. 6 is a simplified diagram of an acne and skin treatment device utilizing energy source and a source of suction to enhance treatment.

As shown in FIG. 6, the device 605, comprises, an energy source 610, deliver energy 620 to the surface of the skin 630. A source providing suction, 640, for example a vacuum pump, 640, delivers a suction to the surface of the skin at the same location that the energy, is applied to 650. The suction can be applied to the skin before during or after the application of energy to the skin. The suction can help clean pore, enhance energy delivery to target tissue and skin components, remove debris, sebum, fat, bacteria, or smoke from the surface, clean pores and hair follicle opening as well as sweat pores, and minimize the sensation of pain. The source of energy 610 can be one of the following: mechanical, thermal, electrical, optical, electromagnetic, ultrasound, microwave, nuclear, chemical, or RF energy. It emits a beam 620 that can be manipulated with lens and mirrors and scanners 635 as well as other optical components 625 or be adapted to directly contact the skin of the user 630.

The device 605 may also comprise in an additional preferred embodiment, an intermediate element capable of converting some energy to thermal energy and conducting the thermal energy to the skin sufficient to open and clean skin pores and follicle openings, treat skin ailments, and improve skin condition and look. The thermal energy thus generated may also be applied in conjunction with the application of suction before during or after the thermal energy or other energy application.

In further preferred embodiments, the device 605 may additionally and preferably comprise an energy removal element, said energy removal element adapted and configured to cool said heating element and/or a skin surface to a temperature of less than about 50.degree C., and an electromagnetic source of energy in the blue to ultraviolet range is also applied to achieve sterilization of the skin. The device 605 can advantageously also incorporate a contact suction head, for example a plurality of suction heads 655 attached with a plurality of tubes 657 to a plurality of vacuum pumps 640 so that the suction is applied to the targeted skin area 650 before during or after the application of energy. An source of coolant, 673, for example a Freon gas container can dispense coolant or control a TEC to cool the target skin, for example through a coolant dispensing tube 677.

Devices and methods can also advantageously comprise: an energy source adapted and configured to provide energy to the skin surface; and a controller adapted and configured to automatically energize the energy source so it heats the skin to a temperature sufficient to treat skin conditions and wrinkles, said device further comprising and intermediate material capable containing a substance capable of absorbing said energy, said absorbing substance arranged in patterns that maximize the penetration of light while at the same time create surface heating on the skin surface. This will allow the deeper penetrating energy to heat from below will the upper surface heating to create heat flow downward from the surface direction. The partial heating of the surface also allow faster healing as smaller portions of the epidermis are damaged. For example, surface heating of the upper layers of the skin can be between about 0% to about 70% and preferably between 3% and 50%.

The intermediate absorbing material may contain a laser absorbing substance arranged in patterns that maximize the penetration of light to depths of between about 100 micrometers to about 1 mm in order to maximize penetration of the light to heat the sebaceous glands and minimize secretion of the sebum. The preferred density for deeper laser light penetration and direct light heating of the upper layers of the skin is between about 0% to about 70% and preferably (if surface heating utilizing the intermediate absorbing material is taken into account) between 3% and 50%. A laser in the blue to ultraviolet range can be used in order to utilize the sterilization effect of these wavelengths, as well as generating heat. The heat generation will be increased due to the increased absorption resulting from the shorter wavelengths. In addition, blue and green to orange wavelengths are more readily absorbed in the hemoglobin in the blood and thus enhance heat generation at the surface of the skin and in layers below the surface.

Various tissue conditions can be effectively treated using a plurality of microscopic treatment zones. In that regard zones can be between 1 micrometer in diameter and 7 mm in diameter, preferably between 20 micrometer and 300 micrometer in diameter, and most preferably between 50 micrometer in diameter and about 250 micrometer in diameter. Zones can advantageously be created in a predetermined treatment pattern, wherein a subset of said plurality of discrete microscopic treatment zones includes individual discrete microscopic treatment zones.

Figure 7:
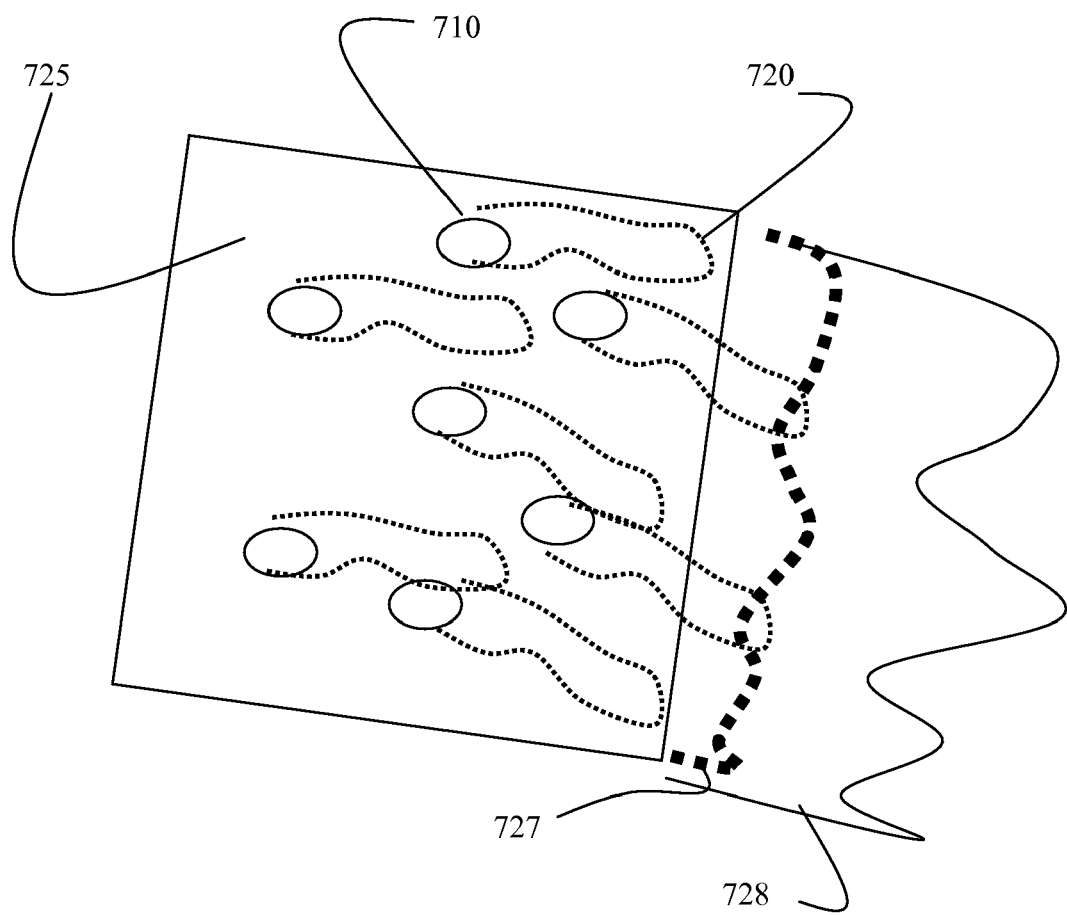
FIG. 7 is a simplified diagram showing a schematic representation of a surface of the skin or tissue treated with a pattern of thermal modification to minimize collateral damage and enhance healing time.

In FIG. 7 a pattern of treated spots 710 in the skin 725, is treated so that at least some tissue modification takes place and wherein the spaces between the spots is not treated. The extent of the spot stretches to a depth 720. The spot diameter of the treated zone is as described above. The percentage of the treated area can advantageously vary from 5% to 95% percent and more preferably from 20% to 80%, and more preferably yet from 30% to 70% and most preferably from 40% to 60%. In especially preferred embodiments, the tissue can be modified in a region extending from the surface to a dept of between about 25 micrometer to about 750 micrometer and more preferably from about 50 micrometer to about 400 micrometer. The percentage of the modified or thermally modified tissue to unchanged tissue is preferably from about 0% to about 70% and preferably and more preferably between 3% and 50%. The dotted line 727 represents the epidermal dermal junction and the line 728 represents the boundaries of the dermis. The depth 720 within which the tissue is modified, thus extend to either the epidermis, dermis, or both.

Thus, specific embodiments and applications of skin treating apparatus and methods have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The invention claimed is:

1. A device for treating a region of intact living skin having a surface and an epidermal/dermal junction, comprising:
    an energy source, wherein the energy source comprises a battery and a capacitor;

a treatment head comprising an electrical resistance heater, a treatment tip comprising an area of between 0.2 cm$^2$ and 2 cm$^2$ configured to be placed against a skin surface, and a layer of electrically insulating but thermally conducting material bonded to the treatment head, wherein the treatment head is configured to provide a thermal energy pulse at the treatment tip responsive to energy provided by the energy source; and a controller that cooperates with the energy source to provide sufficient energy to the electrical resistance heater to heat the treatment tip and thereby create the energy pulse with the treatment head, wherein the controller controls and limits the energy provided to the electrical resistance heater such that the energy is provided to the electrical resistance heater to create an energy pulse having a duration of no more than 100 sec, and the energy pulse delivers an average energy density of 5 J/cm$^2$ or less from the treatment tip, and heats the treatment tip to a temperature of at least 50 degrees Celsius.

2. The device of claim 1 wherein the energy pulse has an energy density of 0.7 J/cm$^2$ to 3 J/cm$^2$.

3. The device of claim 1 wherein the energy pulse has a duration of less than 1 sec.

4. The device of claim 1 wherein the energy pulse has a duration of less than 0.1 sec.

5. The device of claim 1 wherein the controller cooperates with the energy source and treatment head to provide a second energy pulse, wherein the energy pulse and second energy pulse are both provided within a 20 second period.

6. The device of claim 1 wherein the controller cooperates with the energy source and treatment head to provide a second energy pulse with an interpulse delay of between 0.2 sec and 10 sec, inclusive, between the energy pulse and second energy pulse.

7. The device of claim 1 wherein the energy source and the controller are located in a common hand-holdable housing.

8. The device of claim 1 wherein a first side of the layer of electrically insulating but thermally conducting material defines the treatment area.

9. A device comprising:
a hand-holdable housing;
an energy source, wherein the energy source comprises a battery and a capacitor;
a heating element comprising a resistive heater and a treatment tip, wherein the treatment tip comprises an area of between 0.2 cm$^2$ and 2 cm$^2$;
a controller configured to trigger the capacitor to release its discharge capacity to the heating element; and
wherein the capacitor is configured to have a discharge capacity sufficient to provide a thermal energy pulse from the treatment tip of between 0.5 J/cm$^2$ and 5 J/cm$^2$, and to heat the treatment tip to a temperature of at least 50 degrees Celsius.

10. The device of claim 9, further comprising:
a user interface on the hand-holdable housing, wherein the user interface comprises:
a charge button configured to effectuate charging of the capacitor when the charge button is activated by a user;
a fire button configured to cause, when activated by a user, the controller to trigger the capacitor to release its discharge capacity to the heating element.

11. The device of claim 10, wherein the resistive heater comprises a flat conductor.

12. The device of claim 9, wherein the energy source is configured to provide sufficient electrical energy to the heating element to heat the treatment tip to a temperature of at least 70 degrees Celsius.

13. The device of claim 9, wherein the energy source is configured to provide electrical energy to the heating element so as to provide the thermal energy pulse for a duration of no more than 100 seconds.

14. The device of claim 9, wherein the energy source is configured to provide electrical energy to the heating element so as to provide the thermal energy pulse for a duration of no more than 10 seconds.

* * * * *